United States Patent
Cummings et al.

[11] Patent Number: 5,910,125
[45] Date of Patent: *Jun. 8, 1999

[54] COMPOSITE WOUND DRESSING WITH SEPARABLE COMPONENTS

[76] Inventors: Gary Wayne Cummings; Robert Cummings, both of P.O. Box 832616, Richardson, Tex. 75083

[ * ] Notice: This patent is subject to a terminal disclaimer.

[21] Appl. No.: 08/088,625

[22] Filed: Jul. 1, 1993

Related U.S. Application Data

[63] Continuation of application No. 07/780,619, Oct. 23, 1991, abandoned.

[51] Int. Cl.⁶ .............................. A61F 13/00; A61F 15/00
[52] U.S. Cl. .............................. 602/58; 602/59; 128/888; 206/440
[58] Field of Search .................................. 602/41, 42, 47, 602/57, 58, 59; 604/307; 128/887, 888; 206/440, 441

[56] References Cited

U.S. PATENT DOCUMENTS

| | | |
|---|---|---|
| 3,903,882 | 9/1975 | Augurt . |
| 3,954,105 | 5/1976 | Nordby et al. ......................... 128/888 |
| 4,231,357 | 11/1980 | Hessner ..................... 602/47 |
| 4,399,816 | 8/1983 | Spangler ................. 128/154 |
| 4,499,896 | 2/1985 | Heinecke ................... 602/47 |
| 4,561,435 | 12/1985 | McKnight . |
| 4,600,001 | 7/1986 | Gilman ..................................... 604/307 |
| 4,638,796 | 1/1987 | Sims . |
| 4,667,665 | 5/1987 | Blanco et al. . |
| 4,706,662 | 11/1987 | Thompson . |
| 4,826,009 | 5/1989 | Young . |
| 4,846,164 | 7/1989 | Martz ....................................... 602/58 |
| 4,884,563 | 12/1989 | Sessions . |
| 5,056,510 | 10/1991 | Gilman ..................................... 602/57 |
| 5,106,367 | 4/1992 | Gilman ..................................... 602/47 |

OTHER PUBLICATIONS

"Exu–Dry® Wound Dressing" Booklet, Date Unknown, pp. 14, 18.
"Exu–Dry® Wound Dressing on Burn Injuries" Instruction Sheet, Jan., 1989, the sole page.

*Primary Examiner*—Paul B. Prebilic
*Attorney, Agent, or Firm*—Sidley & Austin

[57] ABSTRACT

The dressing system of the present invention provides, in one aspect, a composite dressing that allows a wound to be dressed in one easy step and redressed without disturbing the wound. The composite dressing comprises a contact component having a bottom side facing a wound, and a top side. A dressing component is releasably attached to the top side of the contact component such that the dressing component can be readily separated from the contact component if pulled relative to the contact component. The contact component can remain on the wound to prevent disturbance, and another composite dressing or dressing component can be applied to the contact component.

59 Claims, 5 Drawing Sheets

COMPOSITE WOUND DRESSING WITH SEPARABLE COMPONENTS

This is a continuation of application Ser. No. 07/780,619, filed Oct. 23, 1991, now abandoned.

TECHNICAL FIELD

This invention relates to a wound dressing system for treating wounds. In one aspect, it relates to such a wound dressing system that prevents disturbance of wounds caused by dressing changes.

BACKGROUND OF THE INVENTION

The treatment of wounds with dressings involves a wide variety of situations and applications. A corresponding variety of different types of dressings are available for treating wounds. Dressings have been designed to contain various medicaments and solutions for either absorption into the wound or to wick or remove fluids from the wound area to maintain a proper moisture level at the wound. These dressings typically have some type of absorbent as part of the dressing. Occlusive dressings have been designed to include properties that protect a wound from outside elements, while yet maintain a proper moisture level at the wound and trap the tissue's natural healing fluids. Pressure dressings have been designed to keep pressure on a wound. Body tissues encounter a wide variety of wounds, for example, abrasions, lesions, skin grafts, burns, and pressure sores. Each type of wound undergoes several stages of healing and may require different modes of treatment depending on the stage of healing. Thus, the treatment of a wound involves the selection of a dressing based on the particular type of wound and the various healing stages that are contemplated. Considerations such as size, location and extent of infection of the wound also play a role in selecting a dressing.

However, regardless of the various considerations, the treatment of wounds necessarily involves the periodic changing of the dressings being used to treat the wound. Dressings must be repeatedly removed and replaced for various reasons, for example, to irrigate and cleanse the wound, to reapply medicament, to replace a saturated or soiled dressing, to prevent incorporation of the dressing into the wound, or to merely inspect the wound.

The problem attendant with changing dressings is that the wound is often disturbed during the removal of the dressings. This disturbance of the wound is usually caused when the dressing has wholly or partially adhered to the wound, whereby removal of the dressing destroys any healing that has already occurred, for example, the formation of granulation tissue or the buildup of fibrin which helps clot the blood. Also, and equally as important, removal of an adhered dressing causes great pain to the patient, especially when the wound is at a healing stage where new nerve endings are forming in the wound. The high potential for such wound damage and pain requires extensive nursing time to remove and replace dressings with various techniques to help reduce the wound damage and pain.

The term "adherence" has not been clearly defined in the field of tissue dressings. "Adherence" of a dressing to a wound is typically narrowly defined as when exudate from a wound has dried to and bound with some part of a dressing such as an absorbent. With this narrow definition of adherence in mind, "non-adherent" materials are claimed to have been developed which can be interposed between a wound and a dressing.

Such interposing of "non-adherent" materials has been carried out by two methods. The first method involves a first step of placing a layer of "non-adherent" material over the wound and a second step of placing a separate dressing over the "non-adherent" material. U.S. Pat. No. 4,638,796 to Sims discloses such a method. However, this method involves two application steps and two separate materials to be applied on a wound. The need for sterile dressings and application procedures makes such a two step method appreciably more cumbersome than applying a single dressing. There is also a substantial risk that because of a busy hospital, untrained care providers, or some other mistake or circumstance, the dressing will be applied without first applying the layer of "non-adherent" material. Such an omission could very likely result in the dressing "adhering" to the wound. Another problem with this method is that because of the nature of the "non-adherent" materials, they can be difficult to keep in place while applying the separate dressing. Sometimes the non-adherent materials must be secured in place over the wound before the separate dressing can be applied.

An additional drawback of placing a layer of non-adherent material on the wound and then a dressing over the wound is that, with some types of wounds and some types of dressings, a single layer of non-adherent material will not sufficiently prevent bonding between the wound and the dressing. Applying more than one layer of non-adherent material becomes a cumbersome process in the typical wound care situation. For example, hydrocolloid dressings, such as DuoDERM® made by Convatec®, have a tendency to become very sticky and viscous when in contact with wound exudate. A single layer non-adherent material often does not adequately prevent the hydrocolloid material from working or permeating through the interstices of the non-adherent material and bonding to the wound. If the mesh of the non-adherent material is too tight, liquid may pool at the wound, and be unable to properly pass through the non-adherent material. This creates a potential for maceration of the wound.

The second method of interposing a "non-adherent" material between a wound and dressing involves the use of an integral dressing that has one or more layers of "non-adherent" material laminated or joined to it. This type of dressing is supposed to prevent the wound from "adhering" to the dressing in the narrow sense of the term "adherence", however, redressing a wound with these dressings involves removing the entire dressing, including the "non-adherent" material. U.S. Pat. No. 4,667,665 to Blanco et al. discloses one such dressing: an integral closed dressing with an outer casing that encloses layers of an absorbent and is sealed at its peripheral edges. One side of the dressing casing is two layers of "non-adherent" material. It has been found that removal of these types of dressings without causing pain involves soaking the dressings with a saline solution and then teasing the dressings off of the wound. This process involves intensive nursing time to set up a sterile basin with solution, soak the dressings and then painstakingly tease off the dressings. The soaked dressing presents a disposal problem in that the dressing is dripping wet and often tears apart.

The process of removing these internal dressings can appreciably disturb wounds so as to cause pain and delay healing of the patient. Further, removal of these dressings often requires a qualified care provider to "tease" the dressing off of the wound to minimize disturbance of the wound. As noted above, such teasing and manipulation of these dressings entails additional nursing time as well as additional pain and anxiety that the patient must endure during a dressing change. Sometimes these dressings are torn apart in an effort to prevent removal of a part of the dressing that has adhered to a wound. Such tearing at the wound site is cumbersome, time consuming and often creates a mess as the different layers of the dressings, especially the absorbent, tear apart.

User instructions for the commercial embodiment of the invention disclosed in the Blanco et al. patent disclose an alternate method of removal which requires soaking the dressing, then cutting along its outer edges while the dressing is wet with saline and then peeling away the top layers to leave a layer of "non-adherent" on the wound. Cutting the dressing requires the delicate use of a cutting instrument at the surface of the patient's skin. Again, such a cumbersome task requires intensive nursing time to delicately cut around the dressing edge without accidentally contacting the patient's skin or sensitive wound with the cutting instrument.

A drawback of the so-called "non-adherent" materials is that, although they are "non-adherent" relative to the dressings with which they are used, they are not completely non-adherent. The various types of "non-adherent" material have interstices in which the exudate can dry. Also, in certain situations such as a pressure dressing or a packing dressing, the dressing is pressed onto the treatment area causing the "non-adherent" material to be pressed into the wound so that granulation tissue and epithelial cells are forced into the interstices of the "non-adherent" material. Thus, calling these materials "non-adherent" is a partial misnomer because they can still stick, cling, or otherwise adhere to a wound so as to disturb the wound when such materials are removed.

Thus, a need exists for a dressing system that, regardless of the wound treatment situation, prevents disturbance of wounds caused by dressing changes. Also, a need exists for a dressing system that eliminates the risk that a dressing will be applied, that cannot thereafter be removed without disturbing the wound. Due to the potential for wound disturbance and patient pain caused by dressing changes, care providers are hesitant to remove dressings. A further need exists for a dressing system that eliminates such a potential so that care providers can be free to inspect a wound as often as needed, and dressings can be left on a wound as long as desired or changed as frequently as desired.

Also standardization of the treatment of wounds and simplification of such treatment is much needed. Care providers range from doctors to nurses to inexperienced patients treating themselves. Also, it is very common that the care provider who removes a dressing is not the same care provider who dresses the wound, and thus the care provider removing the dressing will often know nothing about the type of wound or the present healing stage of the wound. Thus, a need exists for a dressing system that provides a dressing that will not harm a wound regardless of the stage of healing of the wound at the time of a dressing change. Further, a need exists for a dressing system that allows such a dressing to be applied in one simple and efficient step, as opposed to a two step treatment.

Care providers often initially treat wounds without knowing if a different dressing or method will ultimately be required and thus a standardized initial treatment of wounds is needed such that once a wound is inspected by a qualified care provider and a decision is made as to the desired treatment, a dressing change can be made easily without fear of disturbing the wound. Thus, a need exists for a dressing system that can be universally used as the initial form of treatment of a wound.

Another aspect of wound treatment is irrigation and cleansing of wounds between dressing changes. Various syringes and bulbs are used by different care providers to irrigate and cleanse wounds. Forces associated with such irrigation and cleansing can harm developing epithelial tissue or otherwise disturb a wound. A need exists for a shield to protect the wound from forces associated with irrigation and cleansing of the wound, and especially a shield that is transparent to readily allow inspection of the wound.

Also, a need exists for a product that has more than one layer of non-adherent material, that can be applied over a wound in one step before a dressing, and that prevents adherence of the dressing to the wound as well as help maintain the proper moisture level at the wound.

One object of the present invention is to provide a dressing system that allows a dressing to be applied in one efficient step and allows redressing of the wound without disturbing the wound. Another object of the present invention is to provide a dressing system that has a built-in precautionary measure, or "safety", that prevents a wound from being disturbed during a dressing change if part of the dressing adheres to the wound. Another object of the present invention is to provide a versatile dressing system that can be used on all types of wounds and wound treatment situations. Another object of the present invention is to provide a dressing system that leaves a "window" to the wound when the dressing is removed and thus allows the wound to be inspected, irrigated and cleansed while at the same time protecting the wound from irrigation forces.

SUMMARY OF THE INVENTION

The present invention provides a dressing system that allows a dressing to be applied in one step and easily changed without disturbing the wound. In accordance with one aspect, the dressing system provides a composite dressing that comprises a contact component having a bottom side for facing the wound, and a top side; and a dressing component disposed on the top side of the contact component and releasably attached to the contact component such that the dressing component can be readily separated from the contact component if purposefully pulled relative to the contact component. In one aspect of the present invention, after the composite dressing is applied to the wound, the dressing component will readily separate from the contact component when pulled, in the event the contact component adheres to the wound. In another aspect of the present invention, after the composite dressing is applied to the wound, the dressing component will readily separate from the contact component when pulled, if the contact component is held in place over the wound while the dressing component is pulled. In another aspect of the present invention, the top side of the contact component is readily accessible by one or more fingers to apply pressure on the contact component to hold it in place, while the dressing component is pulled and separated therefrom.

Another aspect of the dressing system of the present invention provides a method of treating wounds with composite dressings. A composite dressing with a dressing component releasably attached to a contact component is placed over a wound. When the dressing component requires removal or changing, it can be pulled from the wound and readily separated from the contact component. Importantly, in order to redress the wound, another composite dressing can be placed over the old contact component covering the wound, or a new dressing component can be separated from a new composite dressing and placed over the old contact component and the wound. In another aspect of the present invention, a predetermined additional dressing can be applied over the composite dressing.

Another aspect of the dressing system of the present invention is a contact component that provides a "window" to the wound so that the wound can be irrigated, cleansed or inspected with the contact component on the wound, while at the same time the contact component maintains the integrity of the wound during irrigation and cleansing.

The contact component of the composite dressing of the present invention may not require as frequent changing as the dressing component. Thus, to avoid unnecessary disturbance of a wound the dressing component can be readily separated from the contact component. In this way the contact component remains on the wound and protects it from the more frequent removals of the dressing component. Since the contact component may not need to be changed it can remain on the wound through several dressing changes.

If the contact component needs to be changed, it can be carefully removed after the dressing component is first removed. In this manner, the dressing component is not on top of the contact component to interfere with the removal of the contact component. Also, without the dressing component on top of the contact component, removal of the contact component can be facilitated by spraying or rinsing through the contact component so as to quickly "float" the contact component off the wound. If the dressing component remained attached to the contact component, such "floating" would require large volumes of sterile fluid to soak off the dressing. Even if the contact component must be changed as often as the dressing component, the present invention allows the dressing component to be readily removed first to facilitate easier removal of the contact component.

In the preferred embodiment of the present invention, the contact component is sufficiently transparent to allow inspection of the wound and sufficiently permeable to allow irrigation and cleansing of the wound, thus it is contemplated that there will be fewer occasions where the contact component needs to be changed. Also in the preferred embodiment, the contact component maintains the integrity of the wound during dressing changes and can protect the wound from forces associated with various irrigation methods.

Another aspect of the present invention is the provision of an interpositional wafer that comprises three layers of non-adherent material superimposed over each other and joined together. The middle layer has a tighter mesh than the two outer layers so that the wafer both properly controls the moisture level at the wound and prevents adherence between the wound and any dressing placed over the interpositional wafer. The wafer is applied to the wound in one quick step and then any suitable dressing can be placed over the wafer.

BRIEF DESCRIPTION OF THE DRAWINGS

For a more complete understanding of the present invention and for further advantages thereof, reference is now made to the following detailed description of the invention taken in conjunction with accompanying drawings, in which.

DETAILED DESCRIPTION OF THE INVENTION

Figure 1:
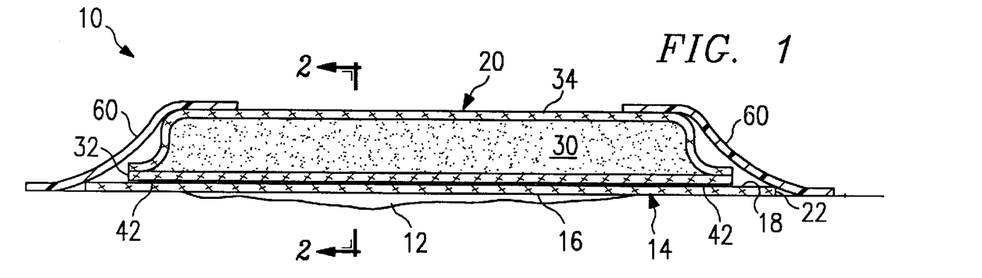
FIG. 1 is a cross-sectional diagram of the preferred embodiment of the composite dressing of the present invention as applied on a wound.

FIG. 1 illustrates the preferred embodiment of the composite dressing 10 of the present invention in place over a wound 12. Composite dressing 10 comprises a dressing component 20 releasably attached to a contact component 14. Contact component 14 has a bottom side 16 facing wound 12 and has a top side 18. Dressing component 20 is disposed on top side 18 and is releasably attached to contact component 14 such that dressing component 20 can be readily separated from contact component 14 if purposefully pulled relative to contact component 14.

Any material, combination of materials or arrangement of materials useful in treating wounds may be used as dressing component 20. Contact component 14 must be sufficiently fluid permeable to allow dressing component 20 to be useful in treating the wound. Thus, any material, combination of materials or arrangement of materials suitable for contact with a wound and that allow the dressing component 20 to be useful in treating wound 12 can be used. Also, materials can be interposed between contact component 14 and dressing component 20 that aid the releasable attachment of the dressing component 20 to the contact component 14 and/or are useful in treating the wound.

Dressing component 20 can be releasably attached to contact component 14 in any manner as long as the dressing component can be readily separated from the contact component. The degree of attachment can vary. For example, the dressing component 20 can be very lightly attached to the contact component 14 so that it remains attached during application of the composite dressing 10 to the wound, yet sufficiently weak that if the contact component 14 adheres even slightly to the wound 12, the dressing component 20 will readily separate from the contact component 14 when pulled from the adhered contact component. Or, in another example, the dressing component 20 can be attached such that the contact component 14 needs to be held in place, for example with a finger or tape, while the dressing component 20 is pulled in order for the components to be readily separated. With either example the contact component 14 does not need to be moved once it is in place on the wound. It can stay in place by either pressing on top side 18 of contact component 14 or by adherence of contact component 14 to wound 12.

For the dressing component 20 to readily separate from the contact component 14, no cutting instrument is required nor does any component of the composite dressing 10 need to be torn or ripped. In the preferred embodiment, the dressing component 20 remains intact while being readily separated from the contact component 14.

In the preferred embodiment, a double faced tape (not shown) is used to releasably attach the dressing component 20 to the contact component 14. A one (1) mil polyester film coated on both sides with a pressure sensitive adhesive. It is presently preferred that one side be coated with an adhesive having 180° peel characteristic of about 40 oz./inch and the other side coated so as to have a lower 180° peel characteristic, for example, about 13 oz./inch. The weaker side is placed against the contact component 14 such that when the dressing component 20 is pulled relative to the contact component 14, the double faced tape will remain on the dressing component 20. A similar degree of releasable attachment can be achieved by using a variety of adhesives, for example, cold seal adhesives, gum adhesives, acrylic adhesives, EVA adhesives, emulsion resins, water or solvent based adhesives, neoprenes, and thermoset powders and resins.

In FIG. 1, dressing component 20 additionally comprises facing sheet 32, an absorbent material 30 and a top sheet 34. As noted above, dressing component 20 is releasably attached to contact component 14 between facing sheet 32 and top side 18. Facing sheet 32 and top sheet 34 can also be any variety of suitable dressing materials, for example, non-woven polymers, netting materials, various plastic sheets perforated with holes, Tega-pore™ by 3M, nylon or polyester monofilament weaves, any Delnet® material, rayon, silk, cotton, impregnated gauze and cellulose derivatives. It should be understood that more than one facing sheet 32, absorbent 30, or top sheet 34 can be employed. For example, multiple facing sheets 32 will affect the moisture level at the wound, different absorbents can be combined to increase absorbing effectiveness, and different top sheets 34 can contribute to stiffness of the composite dressing.

Composite dressing 10 can be held over the wound with a variety of dressing attachments 60. FIG. 1 shows two strips of conventional medical tape. Staples, adhesive, Kerlix®, or other suitable type of wraps or attachments 60 can be used.

Contact component 14 comprises a non-adherent sheet 22, and dressing component 20 is releasably attached to non-adherent sheet 22 with two parallel strips of double faced tape 42 running along opposite sides of dressing component 20. The term "non-adherent" as used herein refers to materials that are non-adherent relative to absorbent materials like gauze because such structure reduces the adherence of exudate to the non-adherent material.

As further shown in FIG. 1, top side 18 extends beyond dressing component 20 to provide a mechanism to apply pressure for holding contact component 14 in place while dressing component 20 is pulled.

Non-adherent sheet 22 is preferably of a type commercially available from Winfield Laboratories, Inc., P.O. Box 832616, Richardson, Tex. 75083 as N-TERFACE brand interpositional surfacing material. Other suitable non-adherent materials can be employed, for example, any Delnet® materials, Tega-pore™ by 3M, non-adherent foams such as Adaptic™ non-adhering dressing by Johnson & Johnson, and impregnated gauze.

The application of composite dressing 10 involves a single step of applying the composite dressing 10 over wound 12. Since the dressing component 20 and the contact component 14 are releasably attached to each other, as opposed to being packaged separately or packaged together but not attached, there is a reduced possibility that a dressing will be applied to a wound without a non-adherent interposed between the wound and the dressing. Since the composite dressing 10 has the contact component 14 which can be left behind on the wound, the composite dressing functions in a sense as a method of insuring placement of a contact component 14 over the wound 12. The attachment between the contact component 14 and dressing component 20 allows the composite dressing 10 to be easily soaked and wrung out before application of the composite dressing to the wound.

Figure 2:
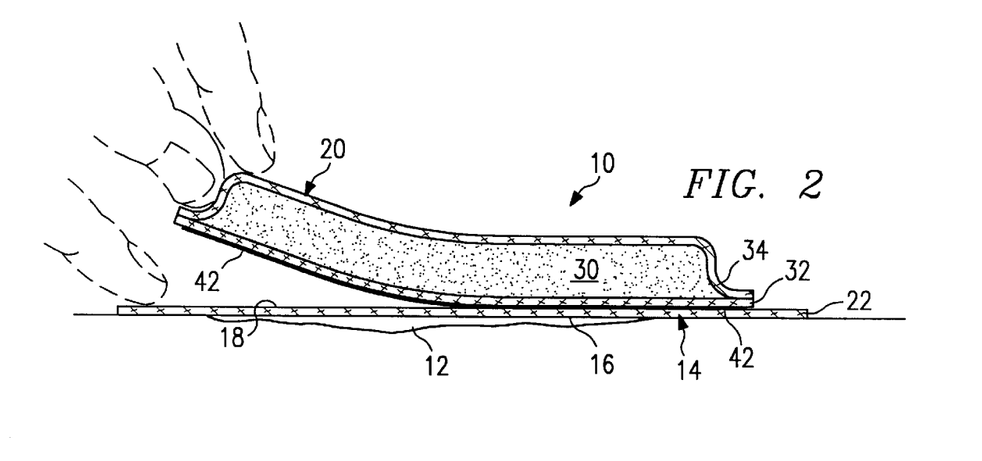
FIG. 2 is a cross-sectional view of FIG. 1, taken along line 2—2 thereof, and further depicting the separation of the dressing component from the contact component.

FIG. 2 illustrates the separation of dressing component 20 from contact component 14. Dressing component 20 can be grasped either manually or with an implement and pulled away from contact component 14. It is preferred that the care provider apply sufficient pressure on the top side of the contact component 14 to hold it in place while the dressing component 20 is removed. This insures that the contact component 14 remains immobile on the wound 12. In an alternative embodiment, the degree of attachment between the dressing component 20 and the contact component 14 can be such that if contact component 14 adheres to wound 12, dressing component 20 will separate from contact component 14 at the interface of the double faced tape 42 without needing to be held by tape or by a finger. In an alternative embodiment, double faced tape 42 has a higher degree of adherence to contact component 14 than to dressing component 20 so that the double faced tape 42 will remain on contact component 14. If wound 12 is to be re-dressed, a new composite dressing can be placed over old contact component 14, or the new contact component of the new composite dressing can be readily removed so that only a new dressing component is placed over old contact component 14. In either case, the intact double faced tape is reused to help retain the new composite dressing or dressing component in place.

After the dressing component 20 is removed, the present dressing system provides a "window" through which the wound can be inspected. Contact component 14 is sufficiently transparent to allow inspection of wound 12, and sufficiently permeable to allow irrigation, cleansing, washing or treatment of wound 12 through contact component 14. Various medicines, ointments or other solutions can also be applied via the permeable contact component 14. Irrigation of a wound often entails the forceful spraying or flushing of a solution over the wound. Such methods can remove and otherwise disrupt delicate epithelial cells. With the "window" on the wound 12 created by the preferred embodiment of the contact component 14, fragile healing tissue is protected from the forces of irrigation and copious irrigation is unnecessary, since this permeable layer is all that is over the wound. These qualities further justify leaving contact component 14 in place over wound 12 for long periods of time while dressing components 20 can be repeatedly dressed over the same contact component.

Another advantage attendant with the ability to leave the contact component on the wound is that, if the contact component 14 needs to be removed from the wound, it is less harmful on the wound 12, and the patient for the care provider to remove the contact component without the dressing component still attached. In the preferred embodiment, the contact component 14 is constructed such that it can be readily floated off the wound by either quickly soaking the contact component 14 or simply peeling it off the wound 12, depending on the healing status of the wound. A conventional dressing requires copious amounts of solution and intensive nursing time to be removed from a wound 12 by soaking. A soaked, conventional dressing presents a disposal problem in that it is generally saturated and dripping with solution mixed with wound exudate and often tears apart due to the weight of the saturated absorbent. With the preferred embodiment of the invention, the dressing component 20 can contain all the needed absorbent and be readily removed from the contact component 14 without needing to be heavily soaked. The contact component 14 left in place has no absorbent and is easily removed and disposed. Also, the bulkiness of conventional dressings detracts from their ability to be readily peeled off a wound and instead must be blindly pulled away from the wound which increases the risk of injury to the wound.

Another advantage of being able to leave the contact component 14 in place on the wound 12 is that when the contact component is transparent, the entire wound can be inspected and observed, which capability enhances the care provider's ability to assess how to further treat the wound or how best to remove the contact component if it needs to be removed. Often there are only one or two points in a wound 12 that create adherence problems and these points can be readily identified and soaked or treated to facilitate painless removal of the contact component 14.

As previously noted, the dressing component 20 is readily removable from the contact component 14 without requiring the use of scissors or dressing shears. The composite dressing 10 is configured such that a care provider can readily retain the contact component over the wound and pull the dressing component. In another aspect, the attachment between the contact component and the dressing component is such that the dressing component will readily separate from the contact component when pulled if the contact component adheres to the wound.

Figure 3:
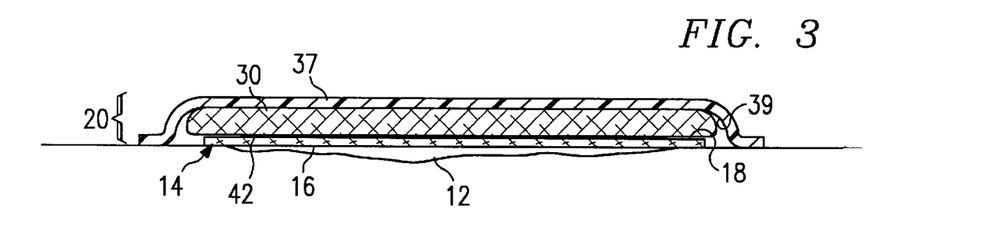
FIG. 3 is a cross-sectional diagram of an alternative embodiment of the composite dressing of the present invention.

FIG. 3 illustrates an alternative embodiment of the composite dressing 10 according to the principles and concepts of the invention. In this embodiment, top side 18 of contact component 14 does not extend beyond dressing component 20, but instead absorbent 30 of dressing component 20 extends beyond contact component 14 to prevent tacky underside 39 of tacky film 37 from coming in contact with contact component 14. Thus, when dressing component 20, comprising absorbent 30 stuck to tacky film 37, is removed, contact component 14 is not pulled up inadvertently by its being stuck to tacky underside 39. If the contact component 14 does not adhere to the wound 12, it will come up with the dressing component 20 due to being attached at double faced tape 42. If the contact component 14 adheres to the wound 12, dressing component 20 will separate at double faced tape 42 when pulled. Dressing component 20 in FIG. 3 can be the product Viasorb® manufactured for Sherwood Medical and disclosed in U.S. Pat. No. 4,561,435 to McKnight et al.

Figure 4:
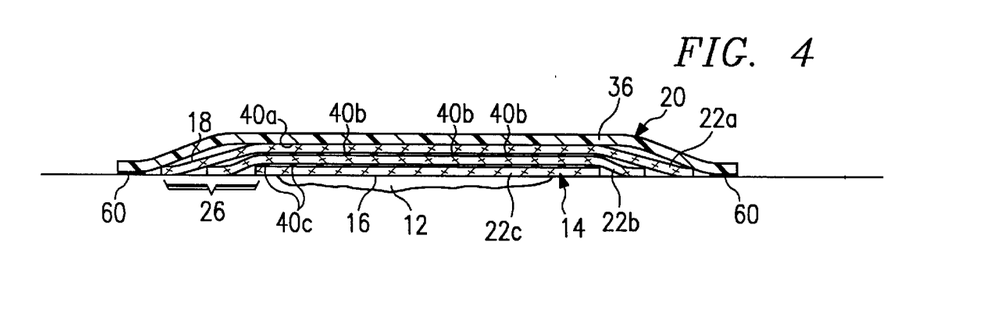
FIG. 4 is a cross-sectional diagram of an alternative embodiment of the composite dressing of the present invention.

FIG. 4 illustrates an alternative embodiment of the composite dressing of the present invention. In this embodiment, contact component 14 comprises a plurality of non-adherent sheets 22a, 22b, 22c, each releasably attached together with respective layers of adhesive 40b and 40c. A layer of adhesive 40a releasably attaches dressing component 20 to the upper non-adherent sheet 22a. These three non-adherent sheets together make up wafer 26. The dressing component 20 comprises an occlusive material 36. Certain wounds and tissue injuries require the use of an occlusive material over the wound 12 to shield the wound from outside elements, yet permit a gas exchange. It may be desired to remove the occlusive material 36 periodically to treat wound 12 with various medicaments or otherwise examine wound 12. The present invention allows for the removal of the occlusive material 36 without disturbing the wound 12 because occlusive material 36 is separable at layers of adhesive 40a, 40b or 40c. Where separation occurs between layers depends on the degree that the wound exudate has penetrated non-adherent sheets 22a, 22b, and 22c. Depending on where separation occurs, the remaining contact component 14 can be 22c; 22c and 22b; or 22c, 22b and 22a. The non-adherent sheets are selected for their affect on wound moisture levels as well has "non-adherent" qualities. This embodiment also illustrates skin attachment means 60 on the underside of dressing component 20. In this embodiment, dressing attachment 60 is an adhesive or tape that allows the sealing of the occlusive material 36 onto the healthy area of skin around wound 12. The occlusive material 36 can be any of a variety of commonly used materials, for example, Opsite®, polyurethane film, microporous polytetra-fluoroethylene (PTFE) membrane, and hydrocolloid materials.

Figure 5:
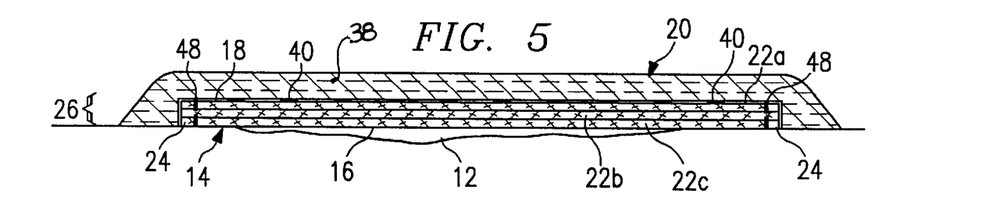
FIG. 5 is a cross-sectional diagram of an alternative embodiment of the composite dressing of the present invention.

FIG. 5 illustrates another alternative embodiment of a composite dressing 10 according to the invention. In this embodiment, contact component 14 comprises a plurality of non-adherent sheets 22a, b, c which comprise wafer 26. Dressing component 20 can be releasably attached to the uppermost non-adherent sheet 22a, while the lowermost non-adherent sheet 22c would be in contact with wound 12. Dressing component 20 in this embodiment is a hydrocolloid material 38. Hydrocolloid materials are commonly employed as a dressing, however, a major drawback of such materials is the propensity to become sticky and bind to a wound. In the embodiment of FIG. 5, wafer 26 helps prevent the hydrocolloid material from coming in contact with the wound. Also the additional non-adherent sheets help maintain the proper moisture level at the wound surface. In this embodiment, non-adherent sheet 22b, which is sandwiched between non-adherent sheets 22a and 22c, is of a different material than non-adherent sheets 22a and 22c. It is presently preferred that non-adherent sheets 22a and 22c are N-TERFACE sheets as described in the preferred embodiment, and non-adherent sheet 22b is of a finer mesh or has a finer pore size than 22a and 22c. A nylon or rayon woven fine mesh or any Delnet® nonwoven material can be used for non-adherent sheet 22b. The non-adherent sheets can be joined with any type of permanent bond 48 in any suitable manner, for example, by ultrasonically bonding the non-adherent sheets along opposite sides. "Permanent" in this respect means that the bonds are not readily separable when in place on the wound 12, but instead require more intensive pulling or manipulation to separate the joined layers and are not intended to function as a release point between the layers. Any suitable hydrocolloid material can be used, for example, DuoDERM® made by Convatec®. Wafer 26 can be used as a contact component with materials other than hydrocolloid materials.

Figure 6:
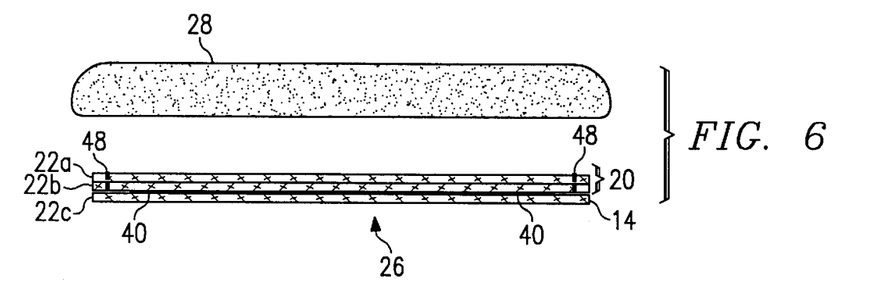
FIG. 6 is a cross-sectional diagram of an alternative embodiment of the composite dressing of the present invention with a predetermined additional dressing.

FIG. 6 illustrates another embodiment of the composite dressing of the invention. In this embodiment, wafer 26 with three non-adherent sheets 22a, 22b and 22c comprise composite dressing 10. Dressing component 20 comprises non-adherent sheets 22a, 22b joined together at oppositely situated permanent bonds 48. Contact component 14 comprises non-adherent sheet 22c releasably attached to non-adherent sheet 22b with adhesive 40. Dressing component 20 is useful in treating wounds by affecting the moisture level at the wound. With this embodiment, an additional dressing 28 can be applied over wafer 26. Wafer 26 defines the composite dressing 10 in this embodiment. The additional dressing 28 can be removed with or without dressing component 20, depending on the extent of any adherence. It should be understood that varying thicknesses and amounts of non-adherent sheets can be used for contact component 14 and dressing component 20.

It should be understood that contact component 14 can be a variety of materials and combinations. For example, contact component 14 can comprise a non-adherent sheet laminated with a hydrophilic material. The hydrophilic material can be used to facilitate the wicking of fluids either away or toward the wound 12. In certain wounds it is desired to wick exudate away from the wound to prevent maceration of the wound caused by excessive moisture. In other applications it may be desired to wick medicaments from dressing component 20 to the wound to keep the wound moist with such medicaments. Any suitable hydrophilic material can be used, for example, polyurethane foams such as Allevyn™. The product Melolite™ of Smith and Nephew and impregnated gauze can also be used as contact components.

Contact component 14 can also be a debridement material. The bottom surface of a bridement material is such that it adheres to a wound, whereby removal of contact component 14 will debride the wound. In many situations it is desired to remove necrotic tissue from a wound, whereupon one method of debridement is to place a dressing over the wound which will adhere to the necrotic tissue and when removed will pull the necrotic tissue away from the wound. It may be desired to leave the debridement material on the wound for a long period of time to allow proper adherence while, at the same time, wicking of exudate away from the wound or transfer of medicaments or moisture to the wound may be desired. In such case dressing component 20 can be releasably attached to contact component 14 and periodically changed while contact component 14 of debridement material is left on the wound to completely adhere to the necrotic tissue. Any suitable debridement material can be used, for example, reticulated polyurethane foam or open celled polyurethane foams or gauze.

Dressing component 20 can also be a variety of materials and combinations. For example, no top sheet may be desired if absorbent 30 needs to be continually soaked, or one continuous sheet may make up the top sheet and facing sheet. Dressing component 20 can be a transcutaneous electrical nerve stimulator or other devices used to electrically or vibrationally stimulate wound healing.

Absorbent 30 used in any embodiment of dressing component 20 can be any of a variety of well known absorbent materials, for example, foams, cellulose matrices, hydrocolloid materials, gauze, seaweed products such as calcium alginanate, cotton, and other suitable natural or manmade fibers. In the preferred embodiment, the absorbent material that is used should be lightweight and should absorb large quantities of fluid without requiring multiple dressing layers. The absorbent should be soft and pliable and readily conform to irregular surfaces ensuring intimate proximation of the dressing with the wound surface to prevent pooling of fluids. The absorbent should be flexible and non-binding to allow for a full range of motion. The absorbent can also be sculptured to fit specific areas of a body.

It is preferable that the absorbent is uniformly structured to wick blood and body fluids away from the wound surface and prevent the pooling of fluids next to the wound to prevent maceration of the wound. The absorbent should breathe and not trap excessive heat. The absorbent can be designed to dispense microencapsulated medication or traditional medication to the wound. The absorbent can be moistened with various medications or solutions prior to application or can be impregnated with a desired medicament. Examples of medicaments that may be absorbed into the absorbent are antimicrobial drugs, analgesics, metal oxides and enzymes, etc. The absorbent can be a hydrocolloidal material. The absorbent should readily wick away any fluids before they dry, thereby helping to prevent any bonding or adherence of the contact component to the wound surface.

The state of technology in this field is presently such that new types of absorbents and dressing materials are continuously being developed. Any type of material and combination of materials can be used as a dressing component as long as it is useful for treating a wound and can be releasably attached to a contact component.

Figure 7:
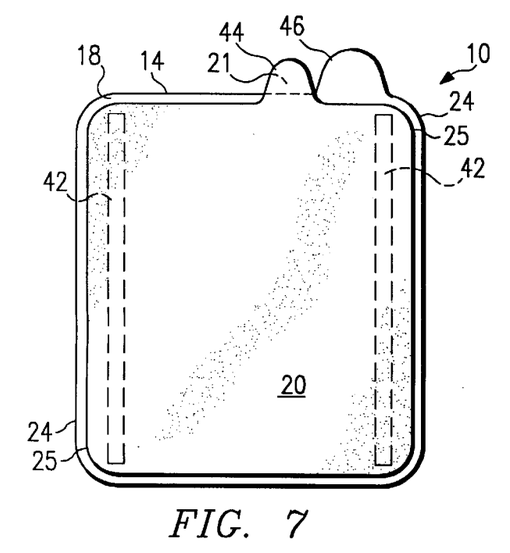
FIG. 7 is a top view of the composite dressing of the present invention.

FIG. 7 is a top view of an embodiment of the composite dressing. Contact component 14 has contact component perimeter 24 and dressing component 20 has dressing component perimeter 25. Top side 18 of contact component 14 extends beyond dressing component perimeter 25. With this configuration, the care provider can easily distinguish dressing component 20 from contact component 14. Moreover, the top side 18 is readily accessible by one or more fingers to apply pressure against the top side of the contact component 14 to prevent accidental pulling of both dressings when attempting to remove the overlying dressing component 20. Contact component 14 can be held in place over the wound by applying pressure on top side 18 manually or with a fastener such as staples, tape or wrap. To further facilitate removal of dressing component 20, FIG. 7 illustrates tab 46 and pull tab 44 extending respectively from contact component 14 and dressing component 20. Tab 46 can be pressed to hold a portion of the contact component 14 in place over the wound. Dressing component 20 is formed with a pull tab 44 having an underside 21. The pull tab 44 is essentially an extension of the material of the dressing component 20 that extends beyond the contact component perimeter 24. Such an extension facilitates grasping dressing component 20 while holding down the tab 46 of the contact component 14. More than one tab 46 or pull tab 44 can be formed on the respective components. These tabs can even be colored differently to further aid in simplification of the process of selecting and removing dressing component 20 relative to contact component 14. Also arrows can be printed on top of the dressing component to indicate the most appropriate direction to remove the dressing component and spaces can be left on the composite dressing for care providers to write down information such as the time the particular dressing component was applied. Also, tags can be attached to either the contact component 14, the dressing component 20 or both on which various information can be written such as when the particular component was placed on the wound and when it should be removed.

Figure 8:
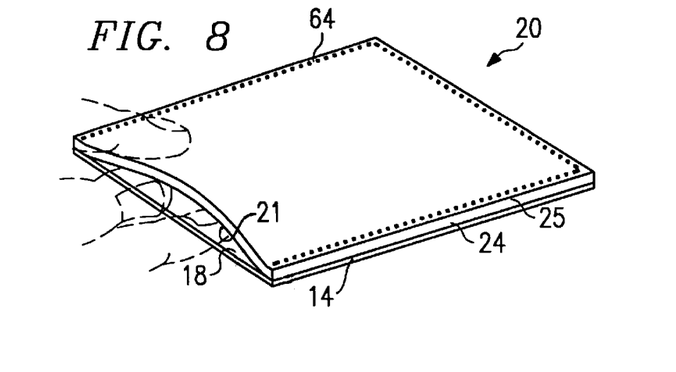
FIG. 8 is an isometric view of an alternative embodiment of the composite dressing of the present invention.

FIG. 8 shows another alternative embodiment of the composite dressing. Contact component 14 has a contact component perimeter 24 and dressing component 20 has a dressing component perimeter 25 coinciding with the contact component perimeter 24. A care provider can readily insert a finger between the two perimeters edges to apply a downward pressure against top side 18 of contact component 14. Dressing component 20 also has an underside 21 which is readily accessible by one or more fingers to facilitate grasping of the dressing component at its perimeter edge. The dressing component 20 can be releasably attached to the contact component along a line of attachment 64. In this embodiment, the line of attachment 64 runs close alongside the perimeters 24 and 25 on three sides leaving a fourth side, or a portion thereof, open to facilitate ready separation. Line of attachment 64 can also be along only two or one sides, or partially on all sides, for example, by leaving one or more corners unattached to allow ready access to top side 18 by a finger. The line of attachment 64 can be formed further away from the perimeter edge and be continuous, in which case there would be sufficient room between the line of attachment and the perimeter edge such that top side 18 is accessible by a finger and dressing component perimeter 25 is graspable. Line of attachment 64 can be created by imparting various types of bonding energy along the line, for example, ultrasonic, irradiation, heat, laser, mechanical deformation, or a mixture thereof.

Figure 9:
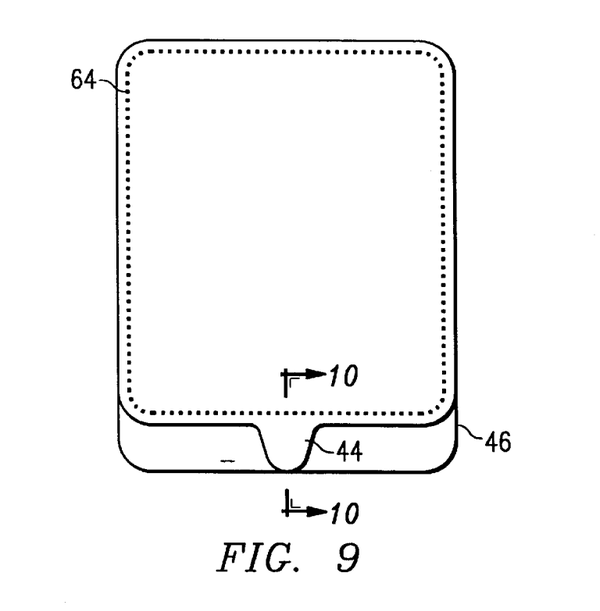
FIG. 9 is a top view of an alternative embodiment of the composite dressing of the present invention.
Figure 10:
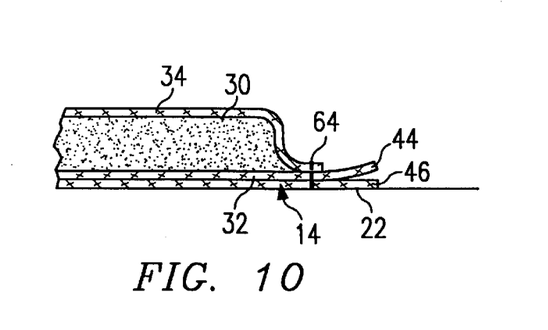
FIG. 10 is a partial cross section of the embodiment of FIG. 9 taken along line 10—10 thereof.

FIGS. 9 and 10 illustrate another alternative embodiment of the composite dressing of the present invention. The top view of FIG. 9 shows tab 46 having a width essentially the same as that of the contact component and extending outwardly beyond the dressing component. A pull tab 44 associated with the dressing component is also shown extending outwardly therefrom. In this embodiment, line of attachment 64 is formed continuously around the perimeter of the composite dressing. FIG. 10, which is a cross-sectional view taken along line 10—10 of FIG. 9, shows dressing component 20 having top sheet 34 joined to facing sheet 32 around absorbent 30 alone line of attachment 64. In this embodiment, line of attachment 64 also serves to attach contact component 14 to dressing component 20. A portion of facing sheet 32 is extended beyond line of attachment 64 to define the pull tab 44. Top sheet 34 can also be similarly extended to be part of pull tab 44. A portion of contact component 14 is extended to create tab 46 which can be held down while pull tab 44 is pulled, thereby breaking line of attachment 64. These tabs allow dressing component 20 to be readily separated from contact component 14. Without any tab 46 or similar extension of contact component 14, line of attachment 64 needs to be sufficiently weak to allow dressing component 20 to separate from contact component 14 when pulled, if contact component 14 should adhere to the wound. With tab 46 or a similar extension, line of attachment 64 can be made stronger because tab 46 allows a care provider to retain the contact component 14 in place when dressing component 20 is pulled and removed. Line of attachment 64 in this embodiment is preferably formed ultrasonically, but can also be formed by irradiation, laser, mechanical deformation, etc.

With the foregoing principles and concepts of the invention in mind, it is contemplated that the dressing disclosed in U.S. Pat. No. 4,667,665 to Blanco et al. can be modified to arrive at the embodiment shown in FIGS. 9 and 10. This can be carried out by adding tabs to the appropriate parts of the dressing such that one tab can be pulled to readily remove the upper portion of the dressing with the absorbent, while pressure is maintained on the other tab to hold the lower sheet in place. While it is preferred to form a tab for each component, the adding of a tab only to the lower sheet can be carried out since the top of the dressing can be pinched and pulled like the embodiment pictured in FIG. 2. The strength of the ultrasonic bond around the perimeter should be such to compromise the integrity of the dressing so as to allow ready separation of the upper portion from the lower sheet.

Even if contact component 14 does not adhere to wound 12 it may still be desired to only remove dressing component 20 and leave contact component 14 in place on the wound. For example, if the wound 12 is to be swabbed with some type of medicament it may be desired to leave contact component 14 in place over the wound to facilitate the spreading of the medicament over the entire surface of the wound while protecting the wound from any discomfort. Also even if contact component 14 is not adhering to a wound, it can help maintain the integrity of newly formed granulation tissue and/or epithelial cells which were beginning to form in the wound. The contact component can also protect the healing cells and tissues from irrigation and cleansing forces.

Figure 11:
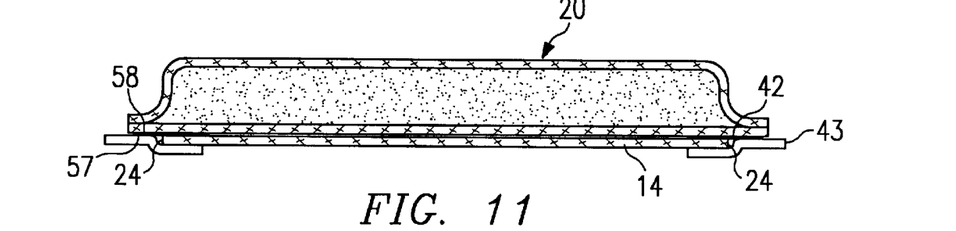
FIG. 11 is a cross-sectional diagram of an alternative embodiment of the composite dressing of the present invention, before application to a wound.
Figure 12:
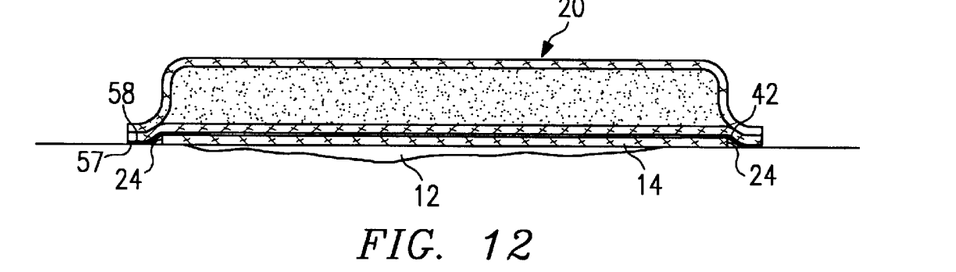
FIG. 12 is a cross-sectional diagram of the embodiment of FIG. 11, as applies on a wound.
Figure 13:
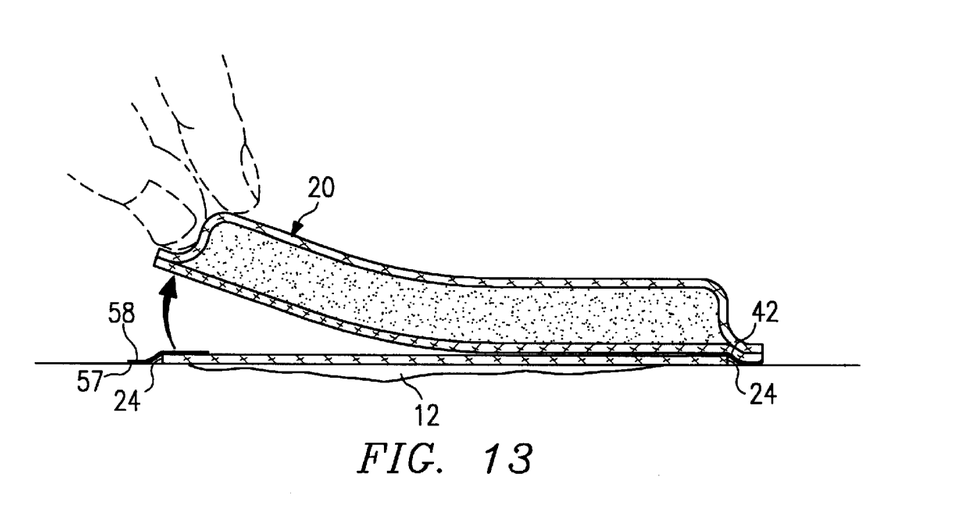
FIG. 13 is a cross-sectional diagram of the embodiment of FIG. 11, showing the dressing component being removed.

FIGS. 11–13 illustrate another embodiment of the composite dressing of the present invention. In this embodiment, an adhesive material such as double faced tape 42 has an adhesive top 58 that releasably attaches dressing component 20 to contact component 14 and has an adhesive bottom 57 which faces the top side of the contact component and extends beyond contact component perimeter 24 to hold contact component 14 in place over wound 12. FIG. 11 illustrates the composite dressing as packaged. Backing strips 43 are used to cover the exposed portion of double faced tape 42. When the composite dressing is ready to be applied to the wound, backing strips 43 are removed and, as FIG. 12 shows, the composite dressing is placed over the wound so that the exposed portions of double faced tape 42 adhere to healthy skin around the wound. When the dressing component is removed, as shown in FIG. 13, double faced tape 42 holds contact component 14 in place over the wound.

Figures 14, 18:
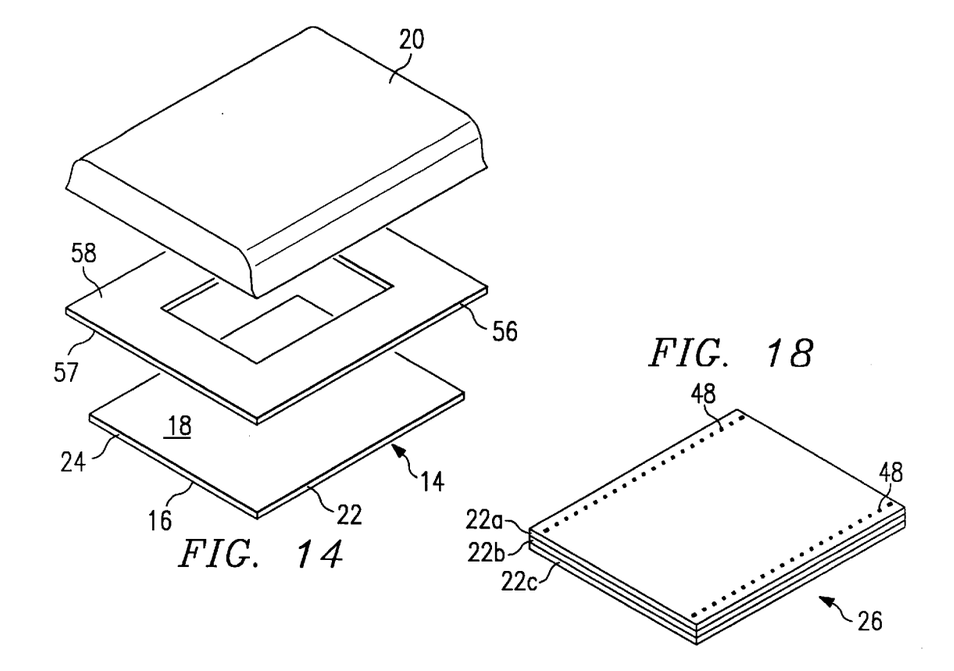
FIG. 14 is an isometric view of an alternative embodiment of the composite dressing of the present invention.
FIG. 18 is an isometric view of a preferred embodiment of the interpositional wafer of the present invention.

FIG. 14 shows a perspective view of an alternative embodiment having an adhesive material 56 with an adhesive bottom 57 and an adhesive top 58. Adhesive top 58 is optional because dressing component 20 can be attached to contact component 14 by other means. Adhesive material 56 has a central square cut-out to facilitate the interaction of the dressing component with the wound. Perforations or a sufficiently permeable adhesive material 56 can also be used in lieu of the cut-out. Adhesive bottom 57 extends beyond contact component perimeter 24.

Figure 15:
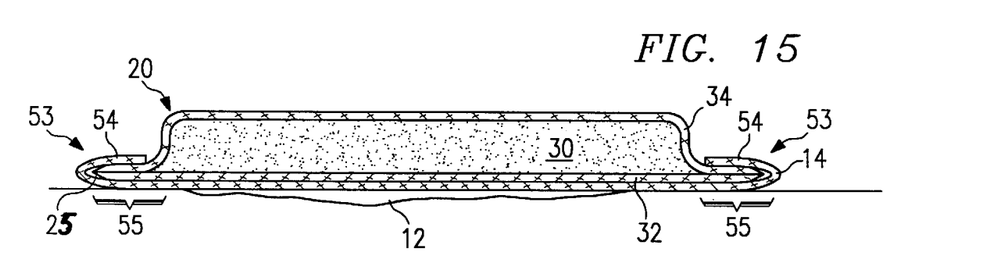
FIG. 15 is a cross-sectional diagram of an alternative embodiment of the composite dressing of the present invention.
Figure 16:
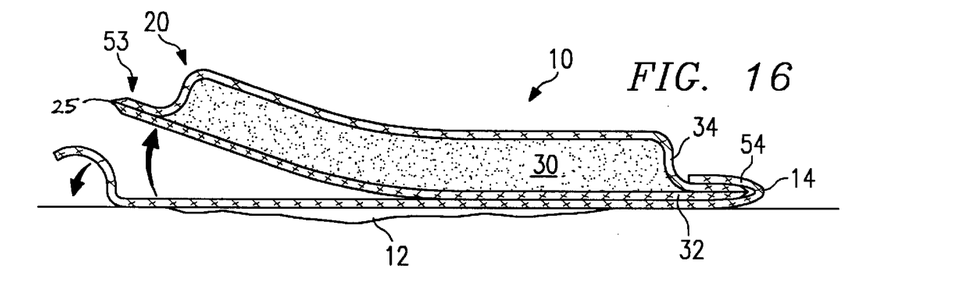
FIG. 16 is a cross-sectional diagram of the embodiment of FIG. 15 depicting the separation of the dressing component from the contact component.

FIGS. 15 and 16 illustrate an alternative embodiment of the present invention. FIG. 15 illustrates an alternative technique to releasably attach dressing component 20 to contact component 14 by folding contact component marginal edge 53 around dressing component perimeter 25 to form fold 54. In this manner, dressing component 20 remains in the folded edge of the contact component 14, yet can become unfolded when pulling on dressing component 20 and if contact component 14 remains adhered to the wound or is held in place over the wound. FIG. 16 illustrates dressing component 20 being separated from contact component 14. Additionally, an adhesive or a double faced tape can be added into fold 54. It should be understood that any style or arrangement of folding can be used if it allows the dressing component to separate from the contact component. Dressing component marginal edge 55 and contact component marginal edge 53 can be folded together upward or downward or one of the marginal edges can be folded around the other component's perimeter.

Any method of mechanically deforming marginal edges 53 and 55 together can be used, for example, crimping, puncturing the marginal edges together with a series of punch holes, or heating plus some type of deforming method.

It should be understood that the dressing component and contact component can be attached to each other at any vicinity between the two components. For example, adhesive or other attachment methods can be randomly distributed across the top side of the composite dressing or lined along opposite sides of its perimeter. In the preferred embodiment, two-sided tape can be run either continuously or intermittently along parallel opposite sides. FIG. 7 illustrates the two parallel strips of tape 42. Any folds or crimps can be formed continuously or intermittently around the perimeter of the composite dressing or only along opposite sides. Also, one or more corners of the composite dressing could be left without any attachment so as to provide a starting point for ready separation of the components. Other means for releasable attachment of the dressing component to the contact component include ultrasonically tacking the dressing component to the contact component, creating an electrostatic attraction between the dressing component and the contact component, heating the contact component and dressing component together, using irradiation or laser techniques, and/or applying pressure to the dressing component and contact component.

The attachment of the dressing component to the contact component allows for the composite dressing to be packaged as a single dressing or product in a single package and sterilized as a single dressing in a single package. When the composite dressing is ready to be used the single sterile package can be opened and the composite dressing is removed with the dressing component and contact component attached to each other so that placement of the composite dressing over the wound is performed in one easy step. When re-dressing a wound that has a contact component remaining thereon, a composite dressing can be removed from its package and the new contact component quickly separated from the dressing component to allow placement of the new dressing component over the old contact component. However, it may be desirable to place the entire composite dressing over the existing contact component in order to help maintain the desired level of moisture at the wound site or as a further precaution against incorporation of material from the dressing component into the wound.

Figure 17:
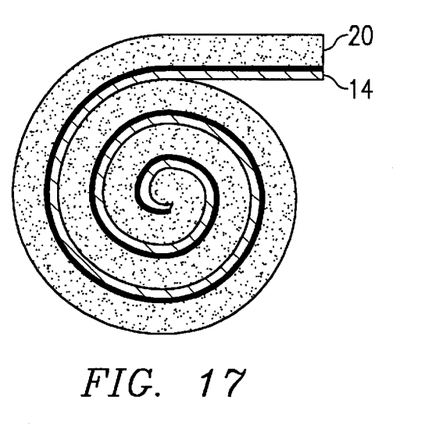
FIG. 17 is an illustration of an alternative embodiment of the composite dressing of the present invention in roll form.

FIG. 17 illustrates an alternative embodiment of the composite dressing in a rolled form. Dressing component 20 and contact component 14 are releasably attached and rolled together.

Another aspect of the present invention comprises a method of treating a wound with a composite dressing. The method comprises the first step of placing a first composite dressing on the wound. The first composite dressing comprises a first contact component for contacting the wound and a first dressing component releasably attached to the first contact component. The second step comprises pulling the dressing component from the wound, whereby if the contact component adheres to the wound and/or is held in place over the wound, the dressing component will separate from the contact component. Alternative and additional steps can be performed, for example, placing a second composite dressing over the wound after the first dressing component has been separated, or in the alternative, the second composite dressing can be split into its two components and the second dressing component can be applied over the first contact component still over the wound. Also, the first contact component can be removed after the first dressing component is removed. Without the first dressing component attached to the first contact component, removal of the first contact component is easier and can be facilitated by rinsing.

FIG. 18 illustrates the preferred embodiment of an interpositional wafer, in accordance with another aspect of the present invention. Wafer 26 in this embodiment can be used alone over a wound to protect the wound, control the moisture level at the wound, and/or facilitate application of various medicaments to the wound. According to this aspect, the wafer is interposed between a wound and a hydrocolloid dressing to prevent the hydrocolloid material from bonding to the wound and to allow a traumatic removal of the hydrocolloid dressing from the wound. The wafer also helps maintain a proper moisture level at the wound underneath the hydrocolloid. The preferred embodiment is the same wafer described in the embodiment of FIG. 5. Wafer 26 comprises three non-adherent sheets 22a, 22b, and 22c. It has been found that when the middle non-adherent sheet 22b has a tighter mesh than 22a and 22c, hydrocolloid material is able to interact with wound 12 but does not stick to wound 12. At the same time the proper level of moisture is maintained at the wound. In the preferred embodiment, outer non-adherent sheets are Delnet® CS-8 distributed by Applied Extrusion Technologies, Inc. Middle sheet 22b is preferably Delnet® CSD0707-25. Any combination of Delnet® materials can be used. Other types of non-adherent materials that can be used in wafer 26 are any non-woven polymer, monofilament weaves, nylon, polyester, rayon, cellulose, Tega-pore™ by 3M, non-adherent foams such as hydrophilic polyurethane foam dressings, Adaptic™ non-adhering dressing by Johnson & Johnson, etc. The non-adherent sheets can be coated with substances to enhance their non-adherent characteristics. The two other sheets do not need to be the same material.

Wafer 26 can be used under any dressing as well as used alone. Wafer 26 can be secured over the wound in any conventional manner. Preferably, the non-adherent sheets are joined by permanent bonds 48 along opposite edges. Any type of process of joining the sheets can be used, for example, ultrasonic, pressure, laser, adhesive, etc. "Permanent" as used herein means that the bonds are not readily separable when the wafer is in place on a wound, but instead require more intensive pulling or manipulation to separate the joined layers.

In practice, wafer 26 is packaged alone or in a pack of several wafers. A wafer is removed from the package and secured over a wound. Then a suitable dressing can be placed over the wafer. When a hydrocolloid dressing is placed over the wafer, removal of the hydrocolloid often pulls up the wafer, but, due to the non-adherent properties of the wafer as well as sufficient moisture at the wound as a result of the wafer, a traumatic removal of the hydrocolloid can be achieved.

Although the present invention has been described with respect to a preferred embodiment and alternative embodiments, various changes, substitutions and modifications of these may be suggested to one skilled in the art, and it is intended that the present invention encompass such changes, substitutions and modifications as fall within the scope of the appended claims.

We claim:

1. A composite dressing applicable to a wound, comprising:
   (a) a contact component constructed of a continuous sheet that covers all portions of the wound over which the contact component is applied, said contact component being pliable and suitable for conforming contact with the surface of the wound such that when the contact component is placed on the wound, the entire surface of the wound beneath the contact component can be comformingly contacted by a bottom side of the contact component, an entire extent of the bottom surface of said contact component being substantially free from adhesives and thus non-adherent to the wound, said contact component also having a top side, and said contact component being constructed of a liquid permeable material to allow permeation of liquids therethrough with respect to the wound; and
   (b) a dressing component adapted for use in treating the wound, said dressing component and said contact component being releasably attached directly to each other such that they can be applied to the wound together in one step and such that, when the bottom side of said contact component is placed in substantially conforming contact with the wound, said contact component is entirely interposed between the surface of the wound underneath the contact component and said dressing component such that liquid can pass between the wound and the dressing component by permeation through said contact component, and said dressing component being releasably attached directly to said contact component such that said dressing component can be readily separated from said contact component when said contact component is in substantially conforming contact with the wound if said dressing component is pulled while said contact component is retained in place on the wound.

2. The composite dressing of claim 1 wherein the degree of attachment between said dressing component and said contact component is such to permit ready separation of said dressing component from said contact component if said contact component adheres to the wound while said dressing component is pulled.

3. The composite dressing of claim 1 wherein the degree of attachment between said dressing component and said contact component is such to permit ready separation of said dressing component from said contact component if said contact component is held in place over the wound while said dressing component is pulled.

4. The composite dressing of claim 3 wherein said contact component is configured so as to permit placement of fasteners selected from the group consisting of tape, adhesive, staples, wrap and a combination thereof over said contact component to hold said contact component in place over the wound.

5. The composite dressing of claim 1 wherein said contact component has a contact component perimeter and said composite dressing further comprises an adhesive material interposed between said contact component and said dressing component, said adhesive material having an adhesive bottom facing said top side of said contact component and extending beyond at least a portion of said contact component perimeter.

6. The composite dressing of claim 5 wherein said adhesive material has an adhesive top facing said dressing component.

7. The composite dressing of claim 3 wherein said contact component is configured to permit application of pressure against said top side of said contact component to hold said contact component in place over the wound.

8. The composite dressing of claim 7 wherein said top side of said contact component is readily accessible by one or more fingers to apply pressure against said top side of said contact component.

9. The composite dressing of claim 8 wherein said dressing component has a dressing component perimeter and said top side of said contact component extends beyond said dressing component perimeter.

10. The composite dressing of claim 8 wherein said contact component has a contact component perimeter and said dressing component has a dressing component perimeter, said dressing component and said contact component oriented relative to each other such that said contact component perimeter and said dressing component perimeter coincide and permit one or more fingers to be readily inserted between said perimeters to apply pressure against said top side of said contact component.

11. The composite dressing of claim 3 further comprising at least one tab extending from said contact component which can be pressed to hold said contact component without pressing on said dressing component.

12. The composite dressing of claim 1 wherein said dressing component has an underside facing towards said contact component, and said dressing component and said contact component being attached together so that said underside is readily accessible by one or more fingers to facilitate grasping said dressing component.

13. The composite dressing of claim 12 wherein said contact component has a contact component perimeter and at least a portion of said underside of said dressing component extends beyond said contact component perimeter.

14. The composite dressing of claim 12 wherein said contact component has a contact component perimeter and said dressing component has a dressing component perimeter, said dressing component and said contact component oriented relative to each other such that said contact component perimeter and said dressing component perimeter coincide and permit one or more fingers to be readily inserted therebetween to facilitate grasping said dressing component at said dressing component perimeter.

15. The composite dressing of claim 3 further comprising at least one pull tab extending from said dressing component.

16. The composite dressing of claim 1 wherein said dressing component is constructed to remain intact while being readily separated from said contact component.

17. The composite dressing of claim 1 wherein said contact component comprises a single non-adherent sheet.

18. The composite dressing of claim 1 wherein said contact component comprises non-adherent sheets superimposed over each other.

19. The composite dressing of claim 18 wherein said non-adherent sheets are of the same material.

20. The composite dressing of claim 18 wherein said non-adherent sheets are releasably attached to each other.

21. The composite dressing of claim 1 wherein said contact component comprises at least one non-adherent sheet joined to a hydrophilic material.

22. The composite dressing of claim 1 wherein said bottom side of said contact component comprises a debridement material that adheres to the wound such that removal of said contact component debrides the wound.

23. The composite dressing of claim 1 wherein said contact component is transparent so as to allow visual inspection of the wound through said contact component.

24. The composite dressing of claim 1 wherein said contact component is constructed of sufficiently permeable material to allow irrigation of the wound through said contact component.

25. The composite dressing of claim 1 wherein said dressing component is absorbent.

26. The composite dressing of claim 25 wherein said dressing component further comprises at least one facing sheet joined to said absorbent and releasably attached to said contact component.

27. The composite dressing of claim 26 wherein said dressing component further comprises at least one top sheet attached over said absorbent opposite said at least one facing sheet.

28. The composite dressing of claim 27 wherein said at least one facing sheet and said at least one top sheet comprise the same material.

29. The composite dressing of claim 1 wherein said dressing component is releasably attached with an adhesive to said top side of said contact component.

30. The composite dressing of claim 29 wherein said adhesive adheres more to said dressing component than to said contact component such that said adhesive remains attached to said dressing component if said dressing component is separated from said contact component.

31. The composite dressing of claim 1 wherein said dressing component is releasably attached to the top side of said contact component with a double faced tape.

32. The composite dressing of claim 31 wherein said double faced tape adheres more to said dressing component than to said contact component such that said double faced tape remains attached to said dressing component if said dressing component is separated from said contact component.

33. The composite dressing of claim 1 wherein said dressing component is releasably attached to said contact component by a bond selected from the group consisting of irradiation, ultrasonic, heat, electrostatic, laser, mechanical deformation, and a mixture thereof.

34. The composite dressing of claim 1 further comprising an additional dressing that is applied over said composite dressing.

35. The composite dressing of claim 34 wherein said contact component comprises one or more contact non-adherent sheets and said dressing component comprises one or more dressing non-adherent sheets.

36. The composite dressing of claim 1 wherein said dressing component has a dressing component marginal edge and said contact component has a contact component marginal edge, and wherein one said marginal edge is folded with respect to the other said marginal edge so as to be releasably attached.

37. The composite dressing of claim 36 wherein said contact component has a contact component perimeter and said dressing component marginal edge is folded around said contact component perimeter.

38. The composite dressing of claim 36 wherein said dressing component has a dressing component perimeter and said contact component marginal edge is folded around said dressing component perimeter.

39. The composite dressing of claim 36 further comprising an adhesive between said dressing component marginal edge and said contact component marginal edge.

40. The composite dressing of claim 1 wherein said dressing component has a dressing component marginal edge and said contact component has a contact component marginal edge that are releasably crimped together.

41. The composite dressing of claim 1 wherein said dressing component is releasably attached to said top side of said contact component.

42. The composite dressing of claim 41 wherein said dressing component has an underside facing said contact component and said underside is releasably attached to said top side of said contact component.

43. A method of treating a wound, comprising the steps of:
(a) placing a first composite dressing having a first contact component and a first dressing component releasably attached directly to each other, on the wound by placing said first contact component in substantially surface conforming contact with the wound, said first contact component being flexible and liquid permeable and having a single, continuously non-adhesive bottom side suitable for surface conforming contact with the wound such that the entire surface of the wound beneath the first contact component is in contact with the bottom side of the first contact component, and said first dressing component adapted for use in treating the wound, said first dressing component releasably attached to said first contact component such that when said first contact component is placed in substantially surface conforming contact with the wound, said first contact component is entirely interposed between the surface of the wound beneath the contact component and said first dressing component such that liquid can pass between the wound and the dressing component by permeation through the contact component, and
(b) removing said first dressing component from said first contact component whereby the first dressing component is separated from the first contact component when said first contact component is held in place over the wound and whereby said first contact component remains in place over the wound when said first contact component is not held in place over the wound.

44. The method of claim 43 further comprising the step of placing a second composite dressing over the wound.

45. The method of claim 43 further comprising the steps of:
(a) separating a second dressing component of a second composite dressing from a second contact component of said second composite dressing; and
(b) placing said separated second dressing component over said first contact component on said wound.

46. The method of claim 43 further comprising the step of first applying pressure directly to at least a portion of said first contact component without initially breaking the releasable attachment thereof to said first dressing component, and then pulling said first dressing component therefrom to break the releasable attachment.

47. A composite dressing applicable to a wound, comprising:
(a) a flexible liquid permeable contact component having a single, continuously planar bottom side suitable for conforming contact with the surface of the wound such that when the bottom side is placed on the wound, the entire surface of the wound beneath the contact component can be conformingly contacted by the single bottom side of the contact component, said contact component also having a top side, and a contact perimeter, said contact component sufficiently liquid permeable to allow permeation of liquids through said contact component; and
(b) a dressing component adapted for use in treating the wound, said dressing component and said contact component being releasably attached directly to each other such that they can be readily applied to the wound together in one step and such that when the bottom side of said contact component is placed in substantially conforming contact with the wound, said contact component is entirely interposed between the surface of the wound beneath the contact component and said dressing components such that liquid will pass between the wound and the dressing component by permeation through the contact component, said dressing component having an underside facing said top side and having a dressing perimeter, said dressing component attached to said contact component along at least one line of attachment such that said dressing component can be readily separated from said contact component approximately along said at least one line of attachment when said contact component is retained in place over the wound, said at least one line of attachment located such that said underside of said dressing component is readily accessible by at least one finger at least one point along said dressing perimeter.

48. The composite dressing of claim 47 wherein said at least one line of attachment is located such that said top side of said contact component is readily accessible by the at least one finger at at least one point along said contact perimeter.

49. The composite dressing of claim 48 wherein said contact component and said dressing component are positioned relative to each other such that said contact perimeter and said dressing perimeter coincide.

50. The composite dressing of claim 47 wherein said at least one line of attachment is created by imparting heat along said at least one line.

51. The composite dressing of claim 50 wherein said heat is imparted while mechanically pressing said contact component and said dressing component together along said at least one line.

52. The composite dressing of claim 51 wherein said heat is imparted continuously along said at least one line.

53. The composite dressing of claim 47 wherein said contact component remains intact when said dressing component is separated from said contact component.

54. The composite dressing of claim 1 wherein the bottom side of the contact component is a non-adherent material.

55. The composite dressing of claim 1 wherein the dressing component has at least one absorbent material such that liquids can permeate through the contact component between said absorbent material and the wound.

56. A method of treating a wound, comprising the steps of:
(a) placing a first composite dressing on the wound, said composite dressing comprising a first contact component contactable with the wound and a first dressing component releasably attached to said contact component;
(b) removing said first dressing component and separating said first dressing component from said first contact component if said first contact component is held in place over the wound; and
(c) placing a second composite dressing over the wound.

57. A method of treating a wound, comprising the steps of:
(a) placing a first composite dressing on the wound, said composite dressing comprising a first contact component contactable with the wound and a first dressing component releasably attached to said contact component;
(b) removing said first dressing component and separating said first dressing component from said first contact component if said first contact component is held in place over the wound;
(c) separating a second dressing component of a second composite dressing from a second contact component of said second composite dressing; and
(d) placing said separated second dressing component over said first contact component on said wound if said first contact component remains on the wound.

58. The method of claim 56 further comprising the step of applying pressure on said first contact component while pulling said first dressing component therefrom.

59. The method of claim 57 further comprising the step of applying pressure on said first contact component while pulling said first dressing component therefrom.

* * * * *